United States Patent
Kaleta (10) Patent No.: US 11,026,787 B2
(45) Date of Patent: Jun. 8, 2021

(54) HEART VALVE HOLDER

(71) Applicant: St. Jude Medical, Cardiology Division, Inc., St. Paul, MN (US)

(72) Inventor: Richard Kaleta, Arden Hills, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 247 days.

(21) Appl. No.: 16/397,376

(22) Filed: Apr. 29, 2019

(65) Prior Publication Data

US 2019/0328520 A1  Oct. 31, 2019

Related U.S. Application Data

(60) Provisional application No. 62/664,401, filed on Apr. 30, 2018.

(51) Int. Cl.
*A61F 2/24* (2006.01)

(52) U.S. Cl.
CPC ............ *A61F 2/2427* (2013.01); *A61F 2/246* (2013.01); *A61F 2/2412* (2013.01); *A61F 2/2463* (2013.01); *A61F 2/2466* (2013.01); *A61F 2220/0075* (2013.01)

(58) Field of Classification Search
CPC .. A61F 2/00; A61F 2/24; A61F 2/2409; A61F 2/2427; A61F 2/0095; A61F 2/2412; A61F 2/2463; A61F 2/2466
See application file for complete search history.

(56) References Cited

U.S. PATENT DOCUMENTS

| | | | |
|---|---|---|---|
| 9,333,076 B1 | 5/2016 | Edquist et al. | |
| 2004/0225356 A1 | 11/2004 | Frater | |
| 2006/0241743 A1* | 10/2006 | Bergin | A61F 2/2409 623/2.11 |
| 2009/0076599 A1 | 3/2009 | Bergin | |
| 2011/0167603 A1* | 7/2011 | Vesely | A61F 2/2427 29/221.6 |
| 2015/0119980 A1* | 4/2015 | Beith | A61F 2/2409 623/2.18 |
| 2015/0313711 A1* | 11/2015 | Chang | A61F 2/243 623/2.11 |

OTHER PUBLICATIONS

Extended European Search Report for Application No. EP 19172035.8 dated Aug. 21, 2019, pp. 1-5.

* cited by examiner

*Primary Examiner* — George J Ulsh
(74) *Attorney, Agent, or Firm* — Lerner, David, Littenberg, Krumholz & Mentlik, LLP (57) ABSTRACT

A holder for a prosthetic heart valve may include a hub having an outer surface extending about a longitudinal axis, a commissure support extending downward from the hub, and a plurality of legs extending outward from the hub in radial directions, each leg having a foot extending in a longitudinal direction. Each foot may have two channels on its outer surface, each channel extending from a closed end at a spaced distance from the bottom of the foot to an open end at the bottom of the foot, and two suture holes each spaced apart from the bottom of the foot and extending between the inner surface and the outer surface of the foot.

20 Claims, 5 Drawing Sheets

HEART VALVE HOLDER

CROSS-REFERENCE TO RELATED APPLICATIONS

This application claims the benefit of the filing date of U.S. Provisional Patent Application No. 62/664,401, filed on Apr. 30, 2018, the disclosure of which is hereby incorporated herein by reference.

BACKGROUND OF THE INVENTION

The present invention relates to prosthetic heart valves, and more particularly to apparatus for use in holding such valves prior to and during implantation of the valve in a patient.

There is increasing interest in prosthetic heart valves that use tissue material for the leaflets of the valve. Such valves tend to be less thrombogenic than mechanical prosthetic heart valves. This may reduce or eliminate the need for a patient who has received such prosthesis to take anticoagulant medication on a long-term basis. Tissue-based heart valves may also have other advantages, such as quieter operation than mechanical valves. Because of the interest in such valves, improvements to them are greatly desired.

Despite the various improvements that have been made to prosthetic heart valves, conventional devices, systems, and methods suffer from some shortcomings. For example, conventional prosthetic heart valve holders may have feet that have too large of a width to permit a physician to place sutures into the valve cuff adjacent the feet. Absence of sutures at certain circumferential locations along the cuff may result in paravalvular leakage of blood around the cuff when the valve is closed, thereby causing negative effects for the patient.

There therefore is a need for further improvements to apparatus for use in holding prosthetic heart valves prior to and during implantation of the valve in a patient. Among other advantages, the present invention may address one or more of these needs.

BRIEF SUMMARY OF THE INVENTION

Described herein is a holder for a prosthetic heart valve. The holder may include a hub having an outer surface extending about a longitudinal axis, a commissure support extending downward from the hub, and a plurality of legs extending outward from the hub in first radial directions. Each leg may have a foot extending in a longitudinal direction generally parallel to the longitudinal axis. Each foot may have an inner surface, an outer surface, and a bottom, and a structure defining two channels on the outer surface of the foot, and defining two suture holes each spaced apart from the bottom of the foot and extending between the inner surface and the outer surface of the foot. Each channel may extend from a closed end at a spaced distance from the bottom of the foot to an open end at the bottom of the foot. Each channel may define a concave inner surface.

Also described herein is a prosthetic heart valve assembly including a prosthetic heart valve and a holder. The prosthetic heart valve may have a frame extending circumferentially about a longitudinal axis and surrounding a central opening, a plurality of valve leaflets disposed in the central opening and affixed to the frame, adjacent lateral ends of the leaflets each defining a commissure, and a cuff affixed to the frame and extending circumferentially about an exterior of the frame. The holder may have a hub, a commissure support extending downward from the hub and having a plurality of support surfaces each in contact with a respective one of the commissures, and a plurality of legs extending outward from the hub in first radial directions. Each leg may have a foot in contact with an upward-facing surface of the cuff.

Each foot may have an inner surface, an outer surface, and a bottom, and a structure defining two channels on the outer surface of the foot, and defining two suture holes each spaced apart from the bottom of the foot and extending between the inner surface and the outer surface of the foot. Each channel may extend from a closed end at a spaced distance from the bottom of the foot to an open end at the bottom of the foot. Each channel may define a concave inner surface. The prosthetic heart valve may be sutured to the holder by at least one suture extending through the suture holes and the cuff at locations adjacent the legs of the holder.

BRIEF DESCRIPTION OF THE DRAWINGS

Various embodiments of the present invention will now be described with reference to the appended drawings. It is to be appreciated that these drawings depict only some embodiments of the invention and are therefore not to be considered limiting of its scope.

DETAILED DESCRIPTION

As used herein, when used in connection with devices for delivering a prosthetic heart valve or other medical device into a patient, the terms "proximal" and "distal" are to be taken as relative to the user of the delivery devices. "Proximal" is to be understood as relatively close to the user, and "distal" is to be understood as relatively farther away from the user. Also as used herein, the terms "generally," "substantially," "approximately," and "about" are intended to mean that slight deviations from absolute are included within the scope of the term so modified.

When used to indicate relative locations within the prosthetic heart valve, the terms "longitudinal" and "vertical" are to be taken as the direction of the axis extending between the inflow end and the outflow end of the stent of the heart valve, along the direction of intended blood flow; the term "flow direction" is to be taken as the direction from the inflow end to the outflow end of the stent of the heart valve, along the direction of intended blood flow; and the terms "above," "below," "high," and "low" are to be taken as relative to the inflow end of the stent. "Above" and "high" are to be understood as relatively farther from the inflow end of the stent in the direction of intended blood flow, and "below" and "low" are to be understood as relatively closer to the inflow end of the stent in the direction of intended blood flow. When used to indicate relative locations within the prosthetic heart valve, the term "circumferential" is to be taken as the direction of rotation about the longitudinal axis of the stent.

Referring to FIGS. 1A-1D, an exemplary conventional holder 10 for a prosthetic heart valve 20 has a substantially cylindrical hub 30, a commissure support 40 extending downward from the bottom 32 of the hub, and a plurality of legs 50 extending from the outer circumferential surface 34 of the hub. The holder 10 has a longitudinal axis A1 that extends in a longitudinal direction L1 of the hub 30. The legs 50 extend from the hub 30 at an angle that is radially outward and downward relative to the longitudinal direction L1 of the hub. The holder 10 may be made of a rigid plastic material such as ultem or polysulfone, for example. A handle 60 configured to be grasped by a user at a grasping portion 61 may be coupled to the top 31 of the hub 30 so that a user may rotate and translate the holder 10. A suture 70 (described further below) may temporarily fasten the prosthetic heart valve 20 to the holder 10 while the prosthetic heart valve is manipulated and deployed into a patient.

The prosthetic heart valve 20 has a rigid frame (e.g., made of titanium; not shown) encapsulated by a cover 22 made, for example, from polyester fabric. A cuff 23 at an inflow end of the cover 22 may encapsulate a flexible ring (e.g., made of silicone; not shown) extending circumferentially about the exterior of the rigid frame in a closed curve shape (e.g., a circle). The prosthetic heart valve 20 has three leaflets 24 (e.g., made of bovine pericardial tissue) that coapt together in a central area of the prosthetic heart valve. The leaflets 24 are attached to the frame via stitching between the leaflets and the cover 22. Lateral ends 25 of the leaflets 24 are attached to the cover 22 at commissures 26 that are supported by posts (not shown) of the rigid frame. In the embodiment shown in FIGS. 1B and 1C, the cuff 23 may have a width W1 between an inner edge 27 and an outer edge 28 of the cuff in radial directions perpendicular to the longitudinal axis A1 of about 2.00 mm to about 2.25 mm. In the embodiment shown in FIGS. 1B and 1C, the diameter of the flow opening through the prosthetic heart valve 20 with the leaflets 24 in an open position is about 19 mm, although in other embodiments, other diameters may be used. It should be noted that while the embodiments herein are described predominantly in connection with their use with a prosthetic aortic valve, the valve 20 could be used to replace a different native valve, such as the pulmonary/tricuspid valve, or a typically bicuspid valve, such as the mitral valve. In some embodiments (e.g., a bicuspid valve design), the prosthetic heart valve 20 may have two leaflets 24.

The prosthetic heart valve 20 is designed to replace a native valve of a patient, such as the pulmonary, mitral, tricuspid, or aortic valve. The prosthetic heart valve 20 may be inserted into a patient whose heart has been stopped, via a thoracotomy or open-heart surgery, for example. The prosthetic heart valve 20, for example, can be configured to be sewn into the native aortic annulus of the patient after removal of the native aortic valve leaflets, with the cuff 23 preferably disposed in a supra-annular position in the ascending aorta above the left ventricle, adjacent the native aortic annulus of the patient. The user may position the prosthetic heart valve 20 with the cuff 23 adjacent the native aortic annulus of the patient, and suturing may be applied to stitch the cuff to the native aortic annulus. The user may place the suturing circumferentially about the cuff 23 between the cuff and the native aortic annulus, using a single continuous suture or a plurality of interrupted sutures. For example, three sutures may be used, each of the three sutures extending around part of the circumference of the cuff 23.

Figure 1A:
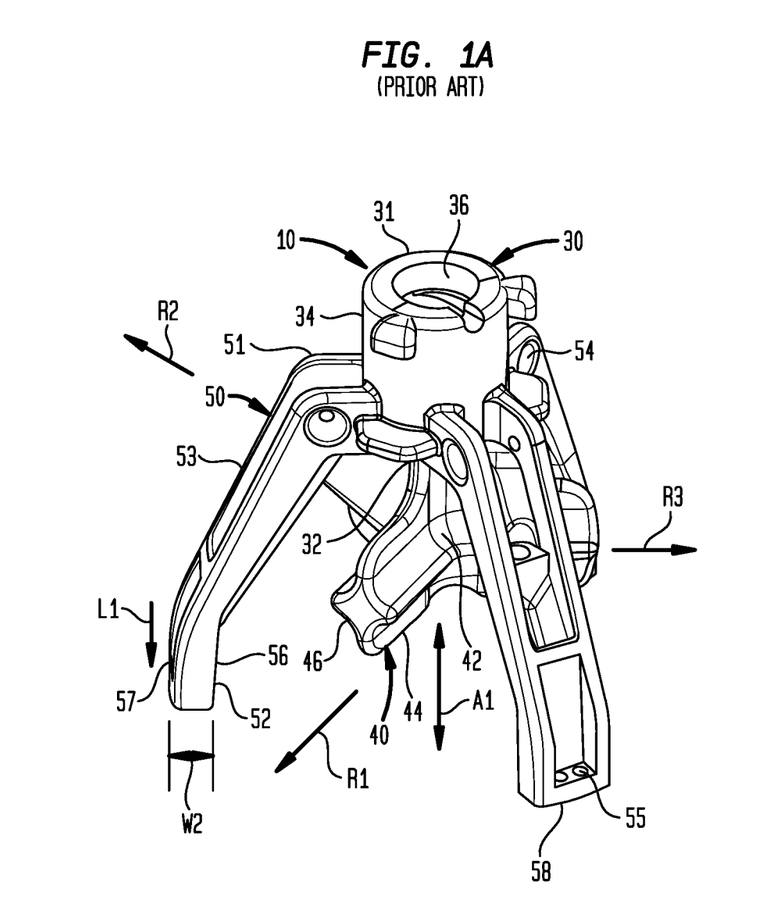
FIG. 1A is a perspective view of a conventional holder for a prosthetic heart valve.

The hub 30 has a substantially cylindrical shape that extends along the longitudinal axis A1 from the top 31 to the bottom 32. The outer circumferential surface 34 extends circumferentially about the longitudinal axis A1 between the top 31 and the bottom 32. The top 31 of the hub 30 has a threaded central opening 36 that is configured to receive a threaded end 62 of the handle 60.

The commissure support 40 has a trunk 42 extending along the longitudinal axis A1 and three arms 44 extending away from the trunk in respective radial directions R1, R2, R3 that are evenly circumferentially spaced about the trunk at about 120° intervals. Each arm 44 has a support surface 46 extending in a plane substantially parallel to the longitudinal direction L1 and substantially perpendicular to the radial direction along which the respective arm extends. Each of the support surfaces 46 is configured to support a respective one of the commissures 26 of the prosthetic heart valve 20. Each support surface 46 is configured to prevent inward deflection of the respective commissure towards the longitudinal axis A1 due to unintentional contact with the user or a portion of the anatomy of a patient during manipulation and insertion of the prosthetic heart valve into the patient.

Each of the plurality of legs 50 has an upper end 51 that extends away from the outer circumferential surface 34 of the hub 30 in respective radial directions R4, R5, R6 that are evenly circumferentially spaced about the hub at about 120° intervals. Each leg 50 is circumferentially located substantially at the midpoint between two adjacent arms 44 about the longitudinal axis A1, so that each leg is located about 60° away from each of the adjacent arms. Each leg 50 has a foot 52 that extends generally parallel to the longitudinal direction L1 and an angled middle section 53 that extends between the upper end 51 and the foot at an angle that is oriented in a direction between the longitudinal direction and the radial directions R4, R5, R6. The upper end 51 of each leg 50 has a suture opening 54 that extends transversely through the leg. A bottom 58 of each foot 52 has two suture holes 55 that extend therethrough substantially in the longitudinal direction. In the embodiment shown in FIGS. 1A-1C, each foot 52 may have a width W2 between an inner surface 56 and an outer surface 57 of the foot in the respective radial direction R4, R5, R6 of about 1.73 mm.

Figure 1B:
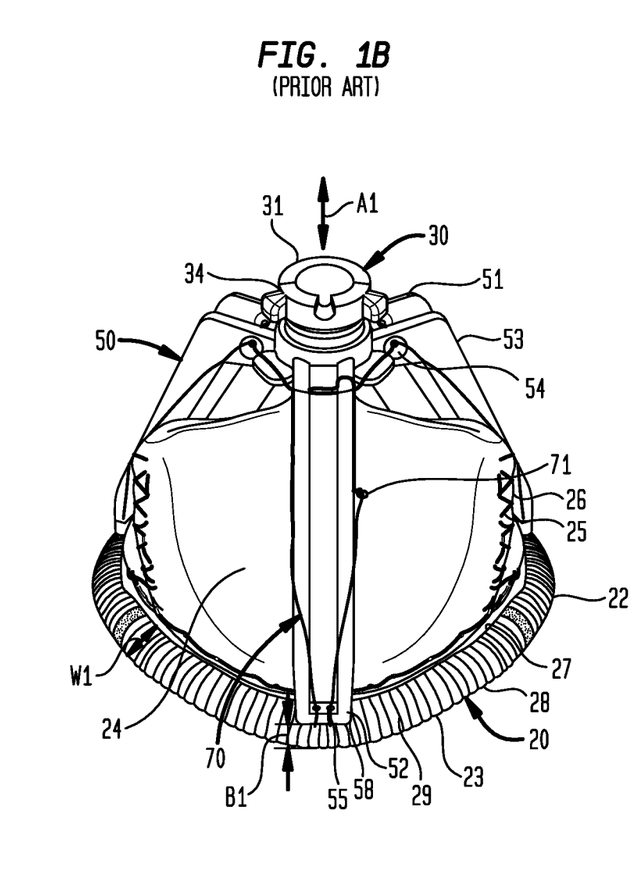
FIG. 1B is a perspective view of the holder of FIG. 1A, shown coupled to a prosthetic heart valve.
Figure 1C:
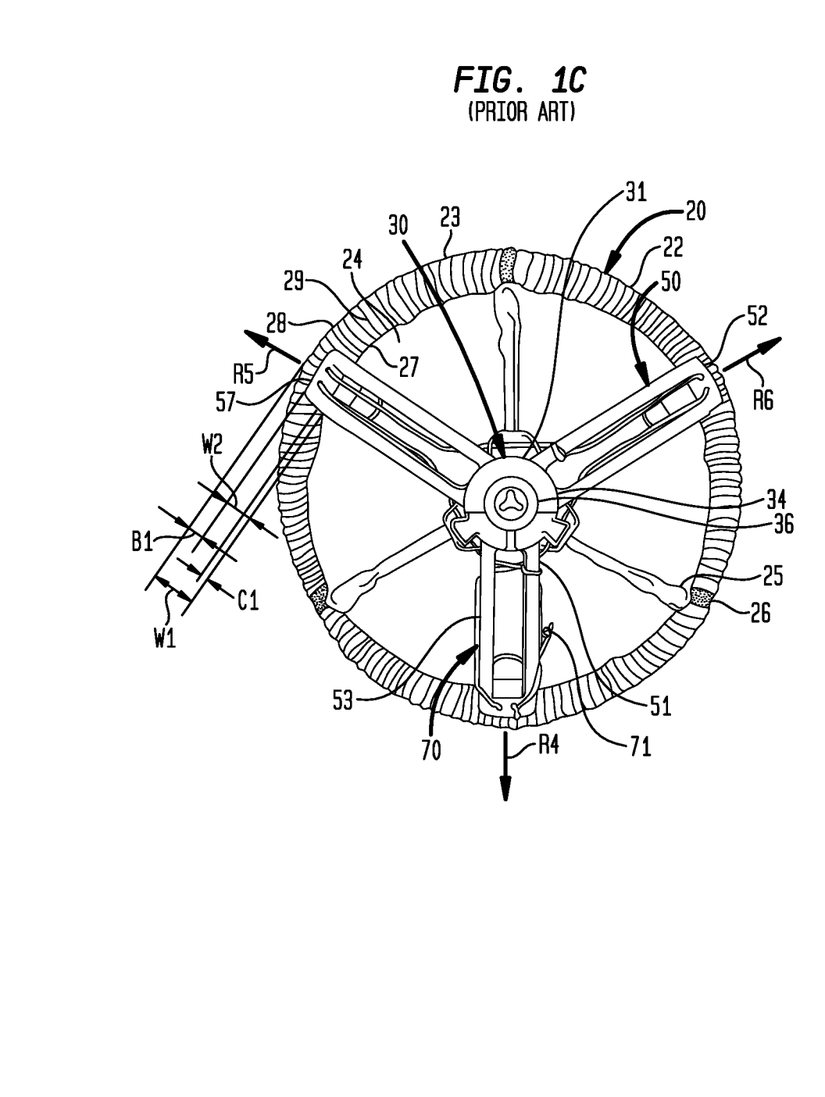
FIG. 1C is a top view of the holder and prosthetic heart valve of FIG. 1B.
Figure 1D:
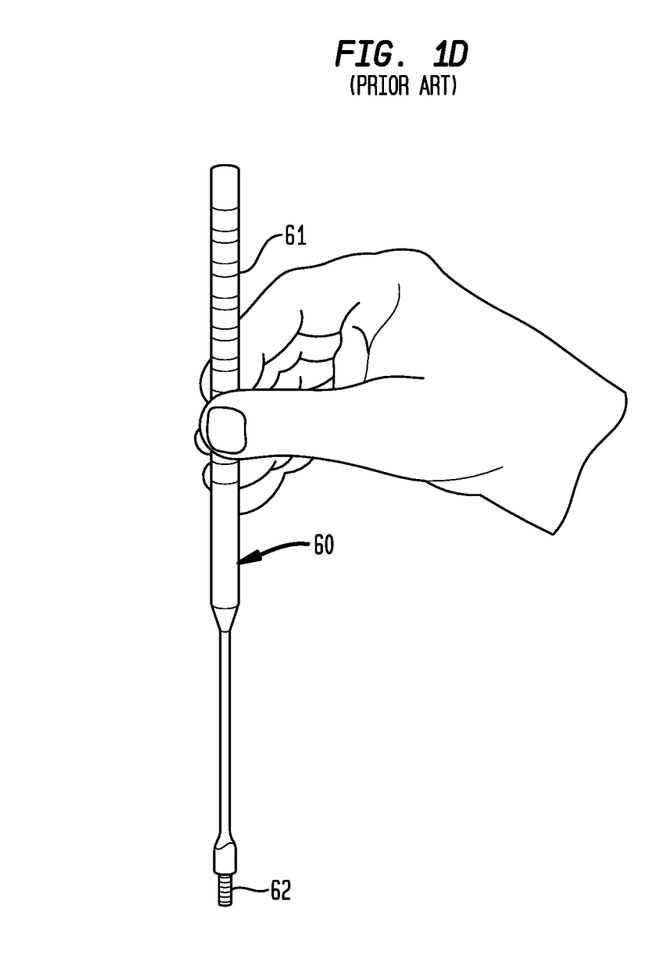
FIG. 1D is a side view of a handle suitable for use with the holder of FIG. 1A.

The prosthetic heart valve 20 may be engaged with and attached to the holder 10 during transport of the prosthetic heart valve into a patient and during suturing of the prosthetic heart valve into the native aortic annulus of the patient. The prosthetic heart valve 20 may be positioned such that the support surfaces 46 of the arms 40 of the holder 10 contact the respective inside surfaces of the commissures 26 of the prosthetic heart valve, such that the legs 50 extend over the outer surfaces of the leaflets 24. The feet 52 of the holder 10 may be placed in contact with an upper-facing surface 29 of the cuff 23 of the prosthetic heart valve 20.

The prosthetic heart valve 20 may be sutured to the holder 10 as shown in FIGS. 1B and 1C. The suture 70 may extend down and up each of the legs 50 and across the outer circumferential surface 34 of the hub 30 between the legs.

As shown, a single suture 70 is used, but alternatively, a plurality of sutures 70 may together fasten the prosthetic heart valve 20 to the holder 10. The suture 70 may extend through a first one of the holes 55, into an interior of the cuff 23 of the prosthetic heart valve 20, out of the cuff and through a second one of the holes. The ends of the suture 70 may be tied to one another in a knot 71 (FIG. 1B). The suture 70 may extend through the suture opening 54 in each of the legs 50 to secure the suture to the upper end 51 of each of the legs.

When the prosthetic heart valve 20 is sutured to the holder 10 as shown in FIGS. 1B and 1C, the position of the feet 52 on the upward-facing surface 29 of the cuff 23 relative to the inner edge 27 and the outer edge 28 of the cuff defines the clearance C1 and the "cuff bite" B1. The width of the upward-facing surface 29 of the cuff 23 between the inner surface 56 of the feet 52 and the inner edge 27 of the cuff in the respective radial direction R4, R5, R6 defines the clearance C1. In other words, the clearance C1 is the amount of radial width of the cuff 23 at the circumferential locations of the feet 52 between the feet and the leaflets 24. An acceptable clearance C1 for preventing the legs 52 from contacting the leaflets 24 when the prosthetic heart valve 20 is sutured to the holder 10 may be about 0.25 mm. The width of the upward-facing surface 29 of the cuff 23 between the outer surface 57 of the feet 52 and the outer edge 28 of the cuff in the respective radial direction R4, R5, R6 defines the cuff bite B1. In other words, the cuff bite B1 is the amount of radial width of the cuff 23 at the circumferential locations of the feet 52 that is available for a suture to "bite" into the cuff during stitching of the cuff to the native annulus of a patient.

The cuff bite B1 may be calculated by subtracting the width W2 of the feet 52 and the clearance C1 between the feet and the leaflets 24 from the width W1 of the cuff 23. For the embodiment shown in FIGS. 1B and 1C, using the exemplary values mentioned above for the width W1 (about 2.00 mm to 2.25 mm) of the cuff 23, the width W2 (about 1.73 mm) of the feet 52, and the clearance C1 (about 0.25 mm), the cuff bite B1 may be between about 0.02 mm and about 0.27 mm. The values of the cuff bite B1 in any particular example will depend on the width W1 of the particular cuff used and how close the geometric center of the prosthetic heart valve 20 is to the longitudinal axis A1 of the holder 10 after the prosthetic heart valve 20 has been stitched to the holder.

In the embodiment shown in FIGS. 1B and 1C, the width W2 of the feet 52 of the holder 10 may be large enough relative to the width W1 of the cuff 23 so that the cuff bite B1 is too small to permit a user to place stitches into the cuff at the same circumferential locations as the feet. If a user cannot place a stitch into the cuff at the same circumferential location as the feet 52, paravalvular leak may occur around the outside of the cuff at the unstitched locations after implantation of the prosthetic heart valve 20. This situation may be addressed by the holder embodiment shown in FIGS. 2A-2F, which will be described below.

Referring to FIGS. 2A-2F, an exemplary holder 110 for a prosthetic heart valve 120 has a substantially cylindrical hub 130, a commissure support 140 extending downward from the bottom 132 of the hub, and a plurality of legs 150 extending from the outer circumferential surface 134 of the hub. The holder 110 has a longitudinal axis A1 that extends in a longitudinal direction L1 of the hub. The legs 150 extend from the hub 130 at an angle that is radially outward and downward relative to the longitudinal direction L1 of the hub. The holder 110 may be made of a rigid plastic material such as ultem or polysulfone, for example. The handle 60 shown in FIG. 1D may be coupled to the top 131 of the hub 130 so that a user may rotate and translate the holder 110. A suture 170 (described further below) may temporarily fasten the prosthetic heart valve 120 to the holder 110 while the prosthetic heart valve is manipulated and deployed into a patient.

Figure 2A:
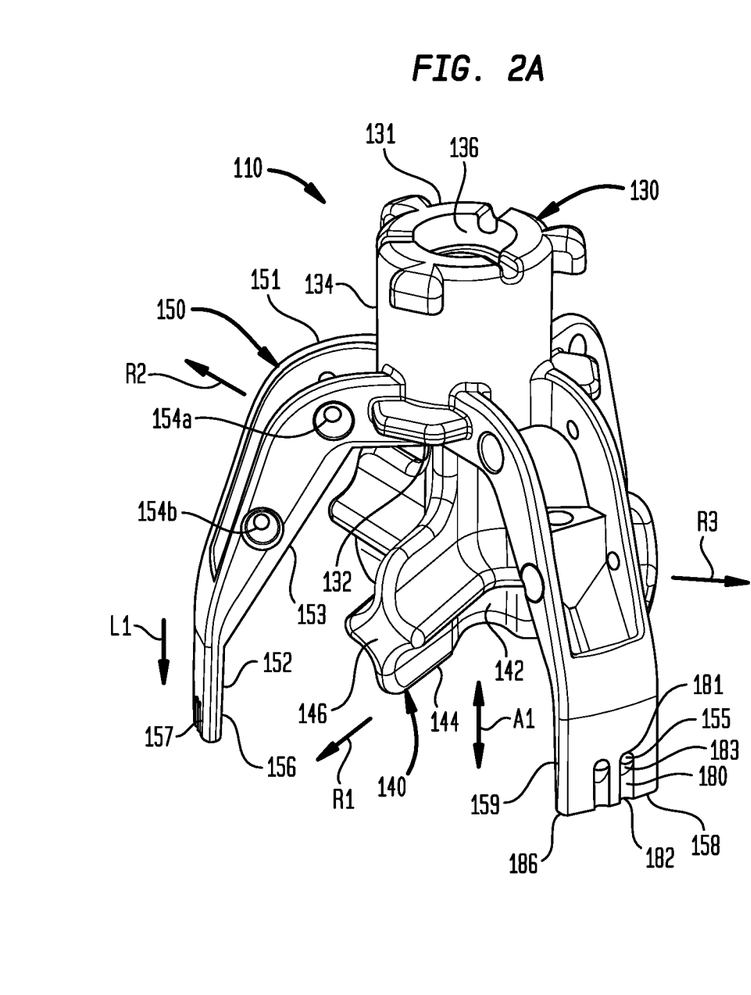
FIG. 2A is a perspective view of a holder for a prosthetic heart valve according to one embodiment of the present disclosure.
Figure 2B:
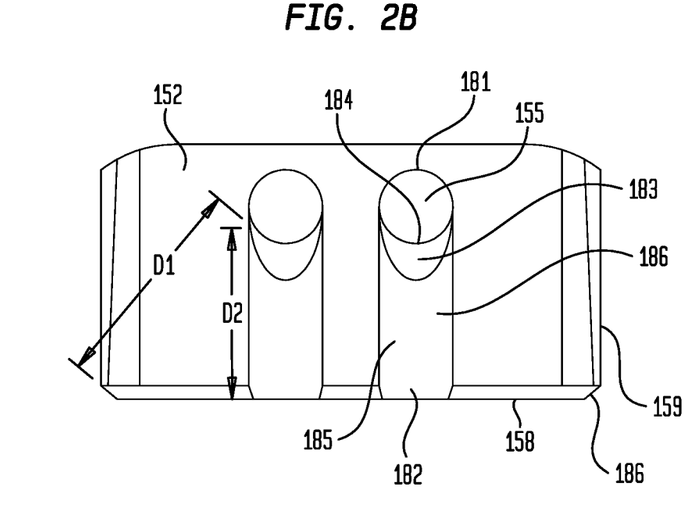
FIG. 2B is a side view of a portion of a leg of the holder of FIG. 2A.
Figure 2C:
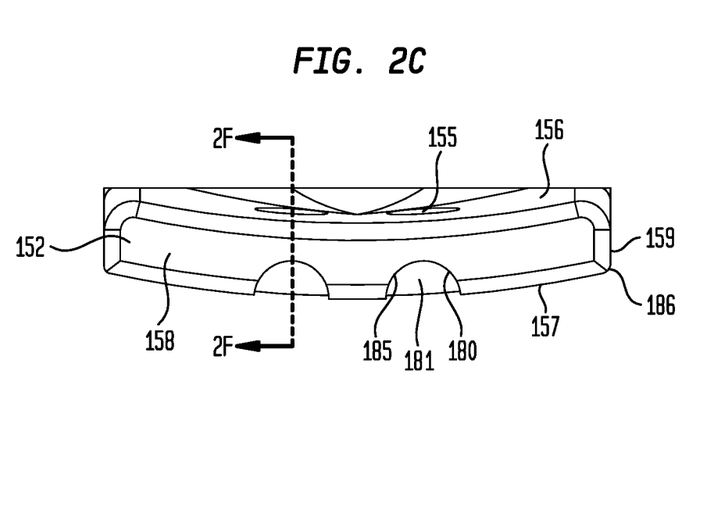
FIG. 2C is a bottom view of the portion of the leg of FIG. 2B.
Figure 2D:
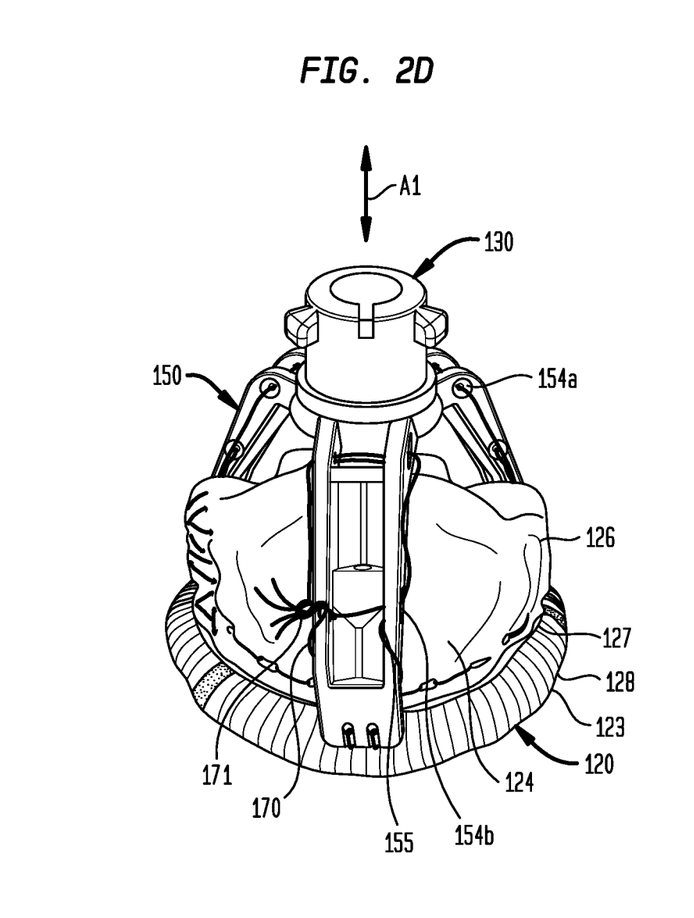
FIG. 2D is a perspective view of the holder of FIG. 2A, shown coupled to a prosthetic heart valve.
Figure 2E:
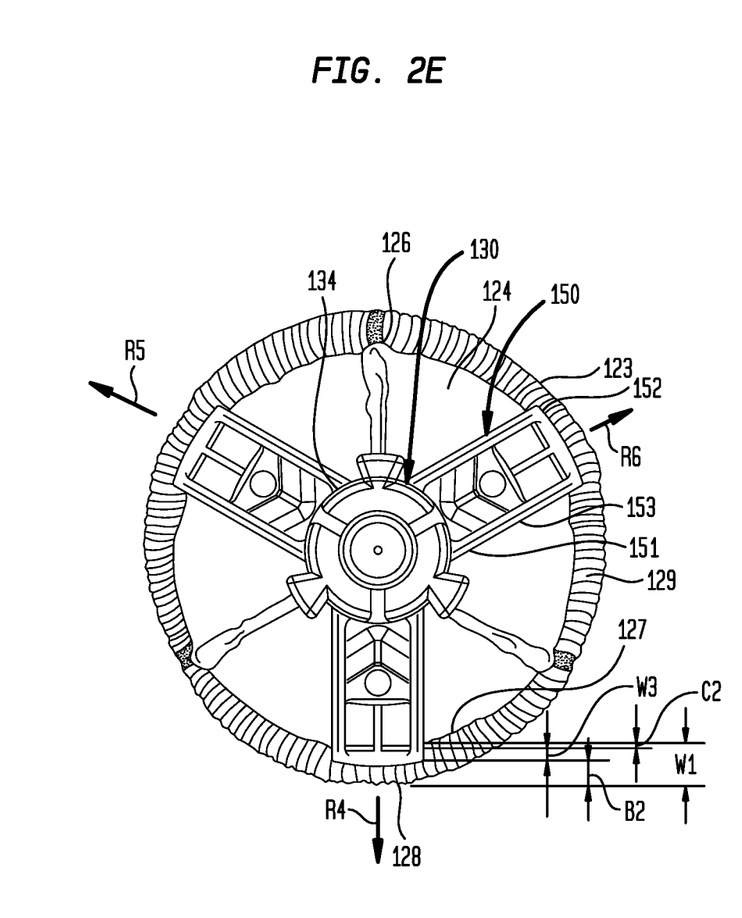
FIG. 2E is a top view of the holder and prosthetic heart valve of FIG. 2D.
Figure 2F:
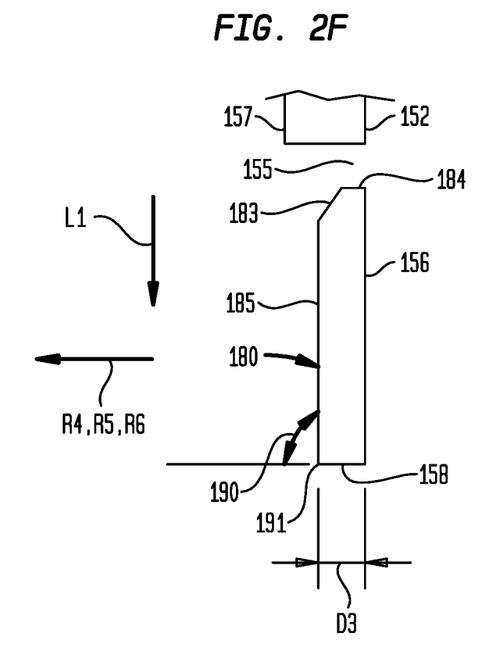
FIG. 2F is a side cross-sectional view of the portion of the leg of FIG. 2B, taken along the line 2F-2F of FIG. 2C.

The prosthetic heart valve 120 has the same features and intended use described above with respect to the prosthetic heart valve 20, except that in the example shown in FIGS. 2D and 2E, the diameter of the flow opening through the prosthetic heat valve 120 with the leaflets 124 in the open position is about 17 mm (in other embodiments, other diameters may be used). In the embodiment shown in FIGS. 2D and 2E, the cuff 123 may have a width W1 between an inner edge 127 and an outer edge 128 of the cuff in radial directions perpendicular to the longitudinal axis A1 of about 2.00 mm to about 2.25 mm.

The hub 130 has a substantially cylindrical shape that extends along the longitudinal axis A1 from the top 131 to the bottom 132. The outer circumferential surface 134 extends circumferentially about the longitudinal axis A1 between the top 131 and the bottom 132. The top 131 of the hub 130 has a threaded central opening 136 that is configured to receive the threaded end 62 of the handle 60.

The commissure support 140 has a trunk 142 extending along the longitudinal axis A1 and three arms 144 extending away from the trunk in respective radial directions R1, R2, R3 that are evenly circumferentially spaced about the trunk at about 120° intervals. Each arm 144 defines a support surface 146 extending in a plane substantially parallel to the longitudinal direction L1 and substantially perpendicular to the radial direction along which the respective arm extends. Each of the support surfaces 146 is configured to support a respective one of the commissures 126 of the prosthetic heart valve 120. Each support surface 146 is configured to prevent inward deflection of the respective commissure towards the longitudinal axis A1 due to unintentional contact with the user or a portion of the anatomy of a patient during manipulation and insertion of the prosthetic heart valve into the patient.

Each of the plurality of legs 150 has an upper end 151 that extends away from the outer circumferential surface 134 of the hub 130 in respective radial directions R4, R5, R6 that are evenly circumferentially spaced about the hub at about 120° intervals. Each leg 150 is circumferentially located substantially at the midpoint between two adjacent arms 144 about the longitudinal axis A1, so that each leg is located about 60° away from each of the adjacent arms. Each leg 150 has a foot 152 that extends generally parallel to the longitudinal direction L1 and an angled middle section 153 that extends between the upper end 151 and the foot at an angle that is oriented in a direction between the longitudinal direction and the radial directions R4, R5, R6. Each leg 150 has two suture openings 154a and 154b that extend transversely through the leg. Each suture opening 154a extends through the upper end 151 of the respective leg 150, and each suture opening 154b extends through the angled middle section 153 of the respective leg.

The foot 152 of each leg 150 has two suture holes 155 that extend therethrough substantially in the respective radial direction R4, R5, or R6 at a position spaced apart from a bottom 158 of the respective foot. In the embodiment shown in FIGS. 2A-2F, each foot 152 may have a width W3 between an inner surface 156 and an outer surface 157 of the foot in the respective radial direction R4, R5, R6 of about 0.66 mm Each suture hole 155 is located within a respective channel 180 that extends substantially in the longitudinal direction L1 on the outer surface 157 of each foot 152. Each suture hole 155 is located at a top end 181 of the respective channel 180, and each channel extends to an open bottom end 182 located at the bottom 158 of the respective foot 152.

As shown, each channel 180 has a concave semi-circular cross-section (FIG. 2C), although other cross-sectional shapes may be used. Each channel has a chamfer 183 to provide an angled transition surface between the inner surface 184 of each suture hole 155 and the concave inner surface 185 of the respective channel 180. The inner surface 185 of each channel 180 extends substantially in the longitudinal direction L1, at an angle 190 relative to the bottom 158 of the respective foot 152. In the example shown in FIG. 2F, the angle 190 is about 90°. The bottom of the longitudinal centerline 191 of the inner surface 185 of each channel 180 is spaced apart from the inner surface 156 of the respective foot 152 by a distance D3.

Each foot 152 has a generally rectangular shape when viewed in the respective radial direction R4, R5, R6 (FIG. 2B). Each channel 180 is spaced apart from a lateral surface 159 of the respective foot 152. Each lateral surface 159 intersects the bottom 158 of the foot at a corner 186, which may be chamfered. The inner surface 184 of each suture hole 155 is located at a distance D1 from the corner 186 of the closest lateral surface 159, and at a distance D2 from the bottom 158 of the foot 152, the distance D1 being greater than the distance D2. The distance D1 preferably is at least 10% greater than the distance D2 so as to prevent the suture 170 from sliding around the closest corner 186 if the suture slips out of its channel 180 due to compression of the cuff 123 and/or stretching of the suture 170.

The prosthetic heart valve 120 may be engaged with and attached to the holder 110 in the same manner described above with respect to the prosthetic heart valve 20, except that in the example shown in FIGS. 2D and 2E, portions of the suture 170 extend circumferentially through the suture holes 155 of the holder and portions of the suture may extend through both of the suture openings 154a, 154b in each of the legs 150 to prevent incidental contact between the suture and the leaflets 124.

When the prosthetic heart valve 120 is sutured to the holder 110 as shown in FIGS. 2D and 2E, the position of the feet 152 on the upward-facing surface 129 of the cuff 123 relative to the inner edge 127 and the outer edge 128 of the cuff defines the clearance C2 and the cuff bite B2. The width of the upward-facing surface 129 of the cuff 123 between the inner surface 156 of the feet 152 and the inner edge 127 of the cuff in the respective radial direction R4, R5, R6 defines the clearance C2. An acceptable clearance C2 for preventing the legs 152 from contacting the leaflets 124 when the prosthetic heart valve 120 is sutured to the holder 110 may be about 0.25 mm. The width of the upward-facing surface 129 of the cuff 123 between the outer surface 157 of the feet 152 and the outer edge 128 of the cuff in the respective radial direction R4, R5, R6 defines the cuff bite B2.

The cuff bite B2 may be calculated by subtracting the width W3 of the feet 152 and the clearance C2 between the feet and the leaflets 124 from the width W1 of the cuff 123. For the embodiment shown in FIGS. 2D and 2E, using the exemplary values mentioned above for the width W1 (about 2.00 mm to 2.25 mm) of the cuff 123, the width W3 (about 0.66 mm) of the feet 152, and the clearance C2 (about 0.25 mm), the cuff bite B2 may be between about 1.09 mm and about 1.34 mm. In one preferred embodiment, the cuff bite B2 may be at least two-fifths of the width W1 of the cuff. In another preferred embodiment, the cuff bite B2 may be at least half of the width W1 of the cuff. The values of the cuff bite B2 in any particular example will depend on the width W1 of the particular cuff used and how close the geometric center of the prosthetic heart valve 120 is to the longitudinal axis A1 of the holder 110 after the prosthetic heart valve has been stitched to the holder.

The larger cuff bite B2 of the embodiment of FIGS. 2D and 2E may have advantages compared to the smaller cuff bite B1 of the embodiment of FIGS. 1B and 1C. The larger cuff bite B2 may permit a user to place stitches into the cuff 123 at the same circumferential locations as the feet 152 when the holder 110 is used to position the prosthetic heart valve 120 adjacent the native aortic annulus of a patient for stitching thereto. The presence of the channels 180 may provide additional space for a user to place stitches into the cuff 123 at the same circumferential locations as the feet 152 when the holder 110 is used to position the prosthetic heart valve 120 adjacent the native aortic annulus of a patient for stitching thereto. These additional stitched locations enabled by the holder 110 may help prevent or lessen paravalvular leak around the outside of the cuff after implantation of the prosthetic heart valve 120.

When the holder 110 is used to position the prosthetic heart valve 120 adjacent the native aortic annulus of a patient for stitching thereto, and a user places stitches into the cuff 123 at the same circumferential locations as the feet 152, a possibility may arise that the user may inadvertently capture one or more portions of the suture 170 and fasten it to the native annulus of the patient. In such a circumstance, it may be more difficult to remove the holder 110 after the prosthetic heart valve 120 has been stitched into the native annulus of the patient since the suture 170 has been captured. This potential circumstance may be addressed by the variant of the holder feet shown in FIG. 3, which will be described below.

Figure 3:
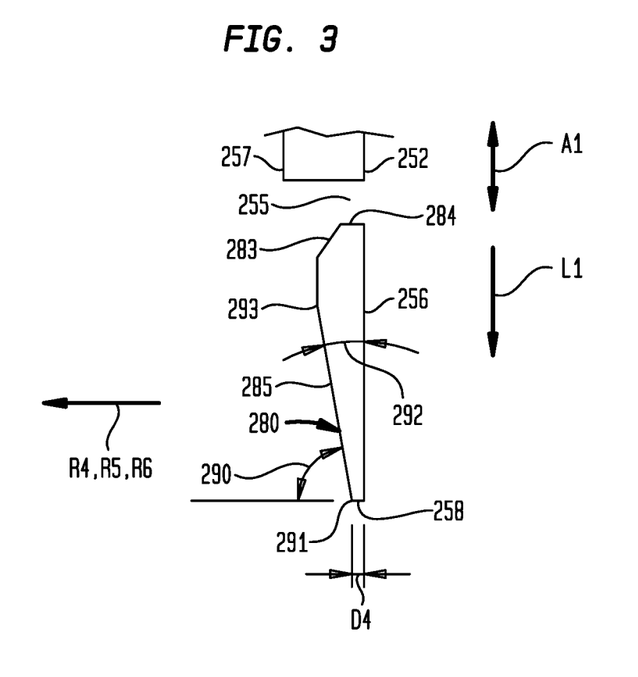
FIG. 3 is a variation of the side cross-sectional view of FIG. 2F, according to an alternative embodiment.

Referring to FIG. 3, each channel 280 of a foot 252 may have a concave semi-circular cross-section extending inward from the outer surface 257 of the foot, in a manner similar to that shown in FIG. 2C, although other cross-sectional shapes may be used. Each channel 280 has a chamfer 283 to provide an angled transition surface between the inner surface 284 of each suture hole 255 and the inner surface 285 of the channel 280 that is medially angled with respect to the longitudinal axis A1. The inner surface 285 of the respective channel 280 extends at an angle 290 relative to the bottom 258 of the foot 252 and at an angle 292 relative to the longitudinal direction L1. In the example shown in FIG. 3, the angle 290 is about 80°, although other angles may be used, such as about 60°, 65°, 70°, 75°, or 85°, for example. The bottom of the longitudinal centerline 291 of the inner surface 285 of each channel 280 is spaced apart from the inner surface 256 of the foot 252 by a distance D4 that is less than the distance D3 shown in FIG. 2F.

In the embodiment shown, the inner surface 285 of each channel extends substantially in the longitudinal direction L1 adjacent the chamfer 283, and then extends at the angle 290 at a starting point 293 spaced apart from the chamfer. However, this need not always be the case. The inner surface 285 may extend at the angle 290 from a location adjacent the chamfer 283 all the way down to the bottom 258 of the foot 252, or the inner surface may extend substantially in the longitudinal direction L1 for any distance between the chamfer and the bottom of the foot before changing direction to the angle 290. It will be appreciated that ordinarily, the longer that the inner surface 285 extends in the longitudinal direction, the larger that the angle 290 will be so that the bottom 258 of the foot 252 can reach the distance D4. The angle 290 may be constant, as shown in FIG. 3, or it may change along the path from the chamfer 283 to the bottom 258 of the foot 252. For example, the angle 290 may begin at about 80° adjacent the chamfer 283, and may gradually increase so that it reaches about 90° at the bottom 258 of the foot 252. Similarly, the angle 290 may begin at about 90° adjacent the chamfer 283, and may gradually decrease so that it reaches about 80° at the bottom 258 of the foot 252.

The smaller distance D4 between the bottom of the longitudinal centerline 291 of the inner surface 285 of each channel 280 and the inner surface 256 of the foot 252 may have advantages compared to the larger distance D3 of the embodiment of FIGS. 2A-2F. In the embodiment of FIG. 3, a suture similar to the suture 170 may be placed closer to the inner surface 256 and farther away from the outer surface 257 of each foot 252, making it less likely that a user placing stitches close to the outer surface of each foot will inadvertently capture one or more portions of the suture and fasten it to the native annulus of the patient when implanting the prosthetic heart valve.

In summary, the disclosure herein describes multiple embodiments of a holder for a prosthetic heart valve. The holder may include a hub having an outer surface extending about a longitudinal axis, a commissure support extending downward from the hub, and a plurality of legs extending outward from the hub in first radial directions. Each leg may have a foot extending in a longitudinal direction generally parallel to the longitudinal axis. Each foot may have an inner surface, an outer surface, and a bottom, a structure defining two channels on the outer surface of the foot, and defining two suture holes each spaced apart from the bottom of the foot and extending between the inner surface and the outer surface of the foot. Each channel may extend from a closed end at a spaced distance from the bottom of the foot to an open end at the bottom of the foot. Each channel may define a concave inner surface; and/or each channel may define a chamfer with an angled transition surface extending between an inner surface of a respective one of the suture holes and the concave inner surface of the channel; and/or the concave inner surface of each channel may extend substantially parallel to the longitudinal axis; and/or the concave inner surface of each channel may extend in a medially angled direction, such that a longitudinal centerline of the concave inner surface at the open end of the channel is closer to the inner surface of the foot than the longitudinal centerline of the concave inner surface at the closed end of the channel; and/or each foot may have first and second lateral surfaces that each intersect the bottom of the foot at a corner, and an inner surface of each of the suture holes may be located a first distance from a closest one of the corners and a second distance from the bottom of the foot, the first distance being greater than the second distance; and/or the first radial directions may be evenly spaced about the longitudinal axis; and/or the commissure support may have a trunk extending generally along the longitudinal axis and a plurality of arms extending outward from the trunk in second radial directions, each arm having a support surface extending in a plane substantially parallel to the longitudinal axis and substantially perpendicular to a respective one of the second radial directions; and/or the second radial directions may alternate with the first radial directions such that each of the second radial directions is offset from two adjacent ones of the first radial directions by about 60°; and/or the hub may define an opening in a top surface thereof, the opening being configured to receive a handle.

Also described herein are multiple embodiments of a prosthetic heart valve assembly including a prosthetic heart valve and a holder. The prosthetic heart valve may have a frame extending circumferentially about a longitudinal axis and surrounding a central opening, a plurality of valve leaflets disposed in the central opening and affixed to the frame, adjacent lateral ends of the leaflets each defining a commissure, and a cuff affixed to the frame and extending circumferentially about an exterior of the frame. The holder may have a hub, a commissure support extending downward from the hub and having a plurality of support surfaces each in contact with a respective one of the commissures, and a plurality of legs extending outward from the hub in first radial directions. Each leg may have a foot in contact with an upward-facing surface of the cuff.

Each foot may have an inner surface, an outer surface, and a bottom, a structure defining two channels on the outer surface of the foot, and defining two suture holes each spaced apart from the bottom of the foot and extending between the inner surface and the outer surface of the foot. Each channel may extend from a closed end at a spaced distance from the bottom of the foot to an open end at the bottom of the foot. Each channel may define a concave inner surface. The prosthetic heart valve may be sutured to the holder by at least one suture extending through the suture holes and the cuff at locations adjacent the legs of the holder; and/or the cuff may be made from a fabric material and encapsulates a flexible ring extending circumferentially through the cuff; and/or the cuff may have a first width between an inner edge and an outer edge thereof, and each foot may have a second width between its inner surface and its outer surface, the first width being at least two times the second width; and/or the assembly may define a clearance between the inner edge of the cuff and the inner surface of each foot, and a cuff bite between the outer edge of the cuff and the outer surface of each foot, the cuff bite being at least half of the first width of the cuff; and/or the prosthetic heart valve may be sutured to the holder by one or more sutures, each of the sutures extending around at least a part of a circumference of the cuff, the sutures together extending through each of the suture holes in each of the feet, through each of the channels in each of the feet, and through portions of the cuff at the locations adjacent the legs of the holder; and/or each of the legs may define two suture openings that extend transversely through the leg, and the sutures together extend through each of the suture openings in each of the legs; and/or each channel may define a chamfer with an angled transition surface extending between an inner surface of a respective one of the suture holes and the concave inner surface of the channel; and/or the concave inner surface of each channel may extend substantially parallel to the longitudinal axis; and/or the concave inner surface of each channel may extend in a medially angled direction, such that a longitudinal centerline of the concave inner surface at the open end of the channel is closer to the inner surface of the foot than the longitudinal centerline of the concave inner surface at the closed end of the channel; and/or each foot may have first and second lateral surfaces that each intersect the bottom of the foot at a corner, and an inner surface of each of the suture holes may be located a first distance from a closest one of the corners and a second distance from the bottom of the foot, the first distance being greater than the second distance; and/or the first radial directions may be evenly spaced about the longitudinal axis; and/or the commissure support may have a trunk extending generally along the longitudinal axis and a plurality of arms extending outward from the trunk in second radial directions, each arm having a respective one of the support surfaces extending in a plane substantially parallel to the longitudinal axis and substantially perpendicular to a respective one of the second radial directions; and/or the second radial directions may alternate with the first radial directions such that each of the second radial directions is offset from two adjacent ones of the first radial directions by about 60°; and/or the hub may define an opening in a top surface thereof, the opening being configured to receive a handle.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A holder for a prosthetic heart valve, the holder comprising:
   a hub having an outer surface extending about a longitudinal axis;
   a commissure support extending downward from the hub; and
   a plurality of legs extending outward from the hub in first radial directions, each leg having a foot extending in a longitudinal direction generally parallel to the longitudinal axis, each foot having:
     an inner surface, an outer surface, and a bottom; and
     a structure defining two channels on the outer surface of the foot, each channel extending from a closed end at a spaced distance from the bottom of the foot to an open end at the bottom of the foot, each channel defining a concave inner surface, the structure further defining two suture holes each spaced apart from the bottom of the foot and extending between the inner surface and the outer surface of the foot.

2. The holder of claim 1, wherein each channel defines a chamfer with an angled transition surface extending between an inner surface of a respective one of the suture holes and the concave inner surface of the channel.

3. The holder of claim 1, wherein the concave inner surface of each channel extends substantially parallel to the longitudinal axis.

4. The holder of claim 1, wherein the concave inner surface of each channel extends in a medially angled direction, such that a longitudinal centerline of the concave inner surface at the open end of the channel is closer to the inner surface of the foot than the longitudinal centerline of the concave inner surface at the closed end of the channel.

5. The holder of claim 1, wherein each foot has first and second lateral surfaces that each intersect the bottom of the foot at a corner, and an inner surface of each of the suture holes is located a first distance from a closest one of the corners and a second distance from the bottom of the foot, the first distance being greater than the second distance.

6. The holder of claim 1, wherein the first radial directions are evenly spaced about the longitudinal axis.

7. The holder of claim 1, wherein the commissure support has a trunk extending generally along the longitudinal axis and a plurality of arms extending outward from the trunk in second radial directions, each arm having a support surface extending in a plane substantially parallel to the longitudinal axis and substantially perpendicular to a respective one of the second radial directions.

8. The holder of claim 1, wherein the second radial directions alternate with the first radial directions such that each of the second radial directions is offset from two adjacent ones of the first radial directions by about 60°.

9. The holder of claim 1, wherein the hub has an opening defined in a top surface thereof, the opening being configured to receive a handle.

10. A prosthetic heart valve assembly, comprising:
    a prosthetic heart valve having a frame extending circumferentially about a longitudinal axis and surrounding a central opening, a plurality of valve leaflets disposed in the central opening and affixed to the frame, adjacent lateral ends of the leaflets each defining a commissure, and a cuff affixed to the frame and extending circumferentially about an exterior of the frame; and
    a holder having a hub, a commissure support extending downward from the hub and having a plurality of support surfaces each in contact with a respective one of the commissures, and a plurality of legs extending outward from the hub in first radial directions, each leg having a foot in contact with an upward-facing surface of the cuff, each foot having:
      an inner surface, an outer surface, and a bottom; and
      a structure defining two channels on the outer surface of the foot, each channel extending from a closed end at a spaced distance from the bottom of the foot to an open end at the bottom of the foot, each channel defining a concave inner surface, the structure further defining two suture holes each spaced apart from the bottom of the foot and extending between the inner surface and the outer surface of the foot,
    wherein the prosthetic heart valve is sutured to the holder by at least one suture extending through the suture holes and the cuff at locations adjacent the legs of the holder.

11. The assembly of claim 10, wherein the cuff is made from a fabric material and encapsulates a flexible ring extending circumferentially through the cuff.

12. The assembly of claim 11, wherein the assembly defines a clearance between the inner edge of the cuff and the inner surface of each foot, and a cuff bite between the outer edge of the cuff and the outer surface of each foot, the cuff bite being at least half of the first width of the cuff.

13. The assembly of claim 10, wherein the cuff has a first width between an inner edge and an outer edge thereof, and each foot has a second width between its inner surface and its outer surface, the first width being at least two times the second width.

14. The assembly of claim 10, wherein the prosthetic heart valve is sutured to the holder by one or more sutures, each of the sutures extending around at least a part of a circumference of the cuff, the sutures together extending through each of the suture holes in each of the feet, through each of the channels in each of the feet, and through portions of the cuff at the locations adjacent the legs of the holder.

15. The assembly of claim 14, wherein each of the legs defines two suture openings that extend transversely through the leg, and the sutures together extend through each of the suture openings defined in each of the legs.

16. The assembly of claim 10, wherein each channel defines a chamfer with an angled transition surface extending between an inner surface of a respective one of the suture holes and the concave inner surface of the channel.

17. The assembly of claim 10, wherein the concave inner surface of each channel extends substantially parallel to the longitudinal axis.

18. The assembly of claim 10, wherein the concave inner surface of each channel extends in a medially angled direction, such that a longitudinal centerline of the concave inner surface at the open end of the channel is closer to the inner surface of the foot than the longitudinal centerline of the concave inner surface at the closed end of the channel.

19. The assembly of claim 10, wherein each foot has first and second lateral surfaces that each intersect the bottom of the foot at a corner, and an inner surface of each of the suture holes is located a first distance from a closest one of the corners and a second distance from the bottom of the foot, the first distance being greater than the second distance.

20. The assembly of claim 10, wherein the commissure support has a trunk extending generally along the longitudinal axis and a plurality of arms extending outward from the trunk in second radial directions, each arm having a respective one of the support surfaces extending in a plane substantially parallel to the longitudinal axis and substantially perpendicular to a respective one of the second radial directions.

* * * * *